(12) United States Patent
Wexler et al.

(10) Patent No.: US 10,113,978 B2
(45) Date of Patent: *Oct. 30, 2018

(54) METHOD FOR MEASURING SOLID-LIQUID INTERFACIAL ELECTRIC FIELD

(71) Applicant: Eastman Kodak Company, Rochester, NY (US)

(72) Inventors: Allan Wexler, Pittsford, NY (US); Steven C. Switalski, Rochester, NY (US); Grace Ann Bennett, Scottsville, NY (US); Kimberly S. Lindner, Rochester, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 207 days.

This patent is subject to a terminal disclaimer.

(21) Appl. No.: 15/221,889

(22) Filed: Jul. 28, 2016

(65) Prior Publication Data

US 2018/0031473 A1 Feb. 1, 2018

(51) Int. Cl.
*G01N 21/64* (2006.01)
*G01N 27/416* (2006.01)
(Continued)

(52) U.S. Cl.
CPC ........... *G01N 21/956* (2013.01); *G01N 21/64* (2013.01); *G01N 21/643* (2013.01); *G01N 21/6428* (2013.01); *G01N 21/91* (2013.01); *G01N 27/4166* (2013.01); *G01N 2021/6421* (2013.01); *G01N 2021/6439* (2013.01); *G01N 2201/12* (2013.01); *Y10T 436/145555* (2015.01)

(58) Field of Classification Search
CPC .. G01N 21/64; G01N 21/6428; G01N 21/643; G01N 2021/6439; G01N 2021/6421; G01N 27/4166; G01N 2201/12; G01N 21/91; G01N 21/956; Y10T 436/145555; Y10T 436/17; Y10T 436/173845; Y10T 436/19; Y10T 436/196666
USPC ... 436/96, 106, 111, 124, 126, 72, 149, 151, 436/164, 166, 172; 422/82.01, 82.05, 422/82.08
See application file for complete search history.

(56) References Cited

U.S. PATENT DOCUMENTS 5,156,918 A   10/1992   Marks et al.
6,331,438 B1   12/2001   Aylott et al.
(Continued)

OTHER PUBLICATIONS

Le Goff et al. Biochimica et Biophysica Acta, vol. 1768, Nov. 7, 2006, pp. 562-570.*

(Continued)

*Primary Examiner* — Maureen Wallenhorst
(74) *Attorney, Agent, or Firm* — Kevin E. Spaulding

(57) ABSTRACT

An interfacial electric field intensity of a surface is measured by covalently binding a monolayer of a voltage sensitive chromophore to the surface and irradiating it with actinic radiation while it is in contact with a liquid and measuring a first fluorescence emission spectrum. A solution of the voltage sensitive chromophore dissolved in a sample of the liquid is also irradiated with actinic radiation and a second fluorescence emission spectrum is measured. The first and second fluorescence emission spectra are compared to determine the interfacial electric field intensity.

10 Claims, 12 Drawing Sheets

(51) Int. Cl.
*G01N 21/956* (2006.01)
*G01N 21/91* (2006.01)

(56) References Cited

U.S. PATENT DOCUMENTS

| | | |
|---|---|---|
| 7,872,468 B2 | 1/2011 | Mitrofanov |
| 2010/0074847 A1 | 3/2010 | Madden et al. |
| 2012/0214193 A1* | 8/2012 | Hattori .............. G01N 21/6428 435/29 |

OTHER PUBLICATIONS

J. Pope et al., "Measurement of electric fields at rough metal surfaces by electrochromism of fluorescent probe molecules embedded in self-assembled monolayers," J. Am. Chem. Soc., vol. 114, pp. 10085-10086, 1992.

P. Fromherz, "Monopole-dipole model for symmetrical solvatochromism of hemicyanine dyes," J. Phys. Chem., vol. 99, pp. 7188-7192, 1995.

J. Pope et al., "Measurements of the potential dependence of electric field magnitudes at an electrode using fluorescent probes in a self-assembled monolayer," J. Electroanalytical Chem., vol. 498, pp. 75-86, 2001.

S. Li et al., "Excluding contact electrification in surface potential measurement using Kelvin probe force microscopy," ACS Nano, vol. 10, pp. 2528-2535, 2016.

H. Xie et al., "Zeta Potential of ion-conductive membranes by streaming current measurements," Langmuir, vol. 27, pp. 4721-4727, 2011.

L. Loew, "Potentiometric dyes: Imaging electrical activity of cell membranes," Pure & Appl. Chem., vol. 68, pp. 1405-1409, 1996.

\* cited by examiner

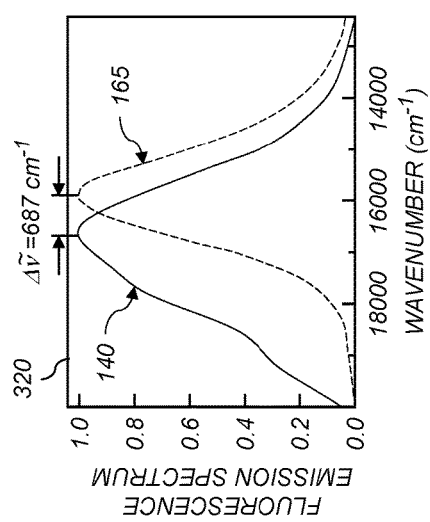
FIG. 3A
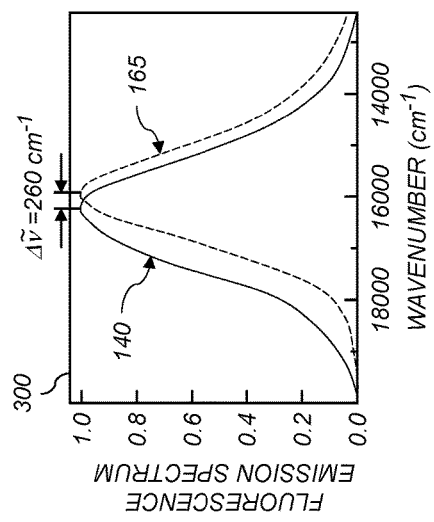
FIG. 3B
FIG. 3C

METHOD FOR MEASURING SOLID-LIQUID INTERFACIAL ELECTRIC FIELD

CROSS-REFERENCE TO RELATED APPLICATIONS

Reference is made to commonly assigned, U.S. patent application Ser. No. 15/221,918 (now U.S. Publication No. 2018/0031474), entitled: "Method for characterizing a liquid," by A. Wexler et al.; to commonly assigned, U.S. patent application Ser. No. 15/221,978 (now U.S. Publication No. 20180031477), entitled: "Method for determining a characteristics difference between liquids," by A. Wexler et al.; and to commonly assigned, U.S. patent application Ser. No. 15/222,000 (now U.S. Publication No. 2018/0031478), entitled: "Surface evaluation system using voltage sensitive chromophore," by A. Wexler et al., each of which is incorporated herein by reference.

FIELD OF THE INVENTION

This invention relates to the determination of solid-liquid interfacial potentials by measuring changes in the fluorescence emission spectrum of a voltage sensitive chromophore affixed to a surface.

BACKGROUND OF THE INVENTION

Voltage sensitive dyes (VSD), also known as potentiometric dyes or voltage sensitive chromophores, have been used to determine membrane potentials for biological cells. Such dyes have been designed to become embedded within a cell membrane orthogonal to the membrane surface where they are then exposed to the membrane electric field. U.S. Patent Application Publication 2010/0074847 to Madden et al., describes the use of chromophore probes for optical imaging of biological materials. The use of voltage sensitive dyes, is also discussed by L. Loew in an article titled "Potentiometric dyes: Imaging electrical activity in cell membranes" (Pure & Appl. Chem., Vol. 68, pp. 1405-1409, 1996). The use is very similar to that described U. S. Patent Application Publication 2010/0074847.

The absorbance or fluorescence emission of a VSD can be measured for the membrane in both the polarized state and un-polarized state. The shift in the resulting spectrum gives the electrical potential difference between the two states.

Two types of VSDs, which vary in their response mechanism, are known. What are considered "slow" VSDs partition within the cell, and their fluorescence intensity is a Nernstian-concentration-dependent response. What are considered "fast" VSD's do not depend on partitioning and instead respond to the electric field directly via the Stark effect.

Experimental strategies for measuring electric field strength (intensity) at charged solid surfaces using a fluorescent dye as a probe particularly in bulk behavior are described by J. Pope et al. in an article entitled "Measurement of electric fields at rough metal surfaces by electrochromism of fluorescent probe molecules embedded in self-assembled monolayers" (J. Am. Chem. Soc., Vol. 114, pp. 10085-10086, 1992), as well as by J. Pope et al. in an article entitled "Measurements of the potential dependence of electric field magnitudes at an electrode using fluorescent probes in a self-assembled monolayer" (J. Electroanalytical Chem., Vol. 498, pp. 75-86, 2001).

U.S. Pat. No. 5,156,918 No. (Marks et al.) describes the use of a poly(phenylene ether) to which a pyridine-terminated chromophore is attached and the resulting nonlinear optical material can be covalently attached to solid surfaces as a monolayer for various purposes.

Surface potential is a key parameter in colloidal and biological sciences governing interactions between materials such as the attractive or repulsive interaction between materials. Thus, adhesion forces between particles or polymers and a surface that affects particle patterning are directly influenced by surface potentials. Such particles and polymers cover a wide range of materials ranging from biological to inorganic materials. Currently there are two prominent methods to determine surface potentials. However, each of these methods create at least one problem. For example, the method of using streaming potentials described by H. Xie et al. in the article "Zeta potential of ion-conductive membranes by streaming current measurements" (Langmuir, Vol. 27, pp. 4721-4727, 2011) requires expensive equipment and the method is damaging to tested samples. Moreover, the use of atomic force microscopy as described by S. Li et al. in the article "Excluding contact electrification in surface potential measurement using Kelvin probe force microscopy" (ACS Nano, Vol. 10, pp. 2528-2535, 2016) is restricted to very small areas and requires long scanning times.

There remains a need for less burdensome and more versatile methods for determining solid-liquid interface electrical field intensities, and for determining the characteristics of liquids.

SUMMARY OF THE INVENTION

The present invention represents a method for measuring an interfacial electric field intensity, including:

providing a surface having a reactive carbocyclic aromatic linking group covalently attached thereon;

providing a voltage sensitive chromophore precursor including a p substituted dialkylamino aryl group that is conjugatively linked to a terminal N containing heterocyclic aromatic group;

reacting the voltage sensitive chromophore precursor with the reactive carbocyclic aromatic linking group that is covalently attached to the surface to form a monolayer of a voltage sensitive chromophore that is covalently bound to the surface;

irradiating the monolayer of the covalently bound voltage sensitive chromophore with actinic radiation while it is in contact with a liquid and measuring a first fluorescence emission spectrum;

providing a voltage sensitive chromophore solution of the voltage sensitive chromophore dissolved in a sample of the liquid;

irradiating the voltage sensitive chromophore solution with actinic radiation and measuring a second fluorescence emission spectrum; and comparing the first and second fluorescence emission spectra to determine an interfacial electric field intensity.

This invention has the advantage that in provides a method for directly measuring the interfacial electric field intensity at an interface between a solid and a liquid.

It has the additional advantage that the fluorescence emission spectra can be measured for a lattice of spatial positions on the surface to inspect defects or features on the surface.

BRIEF DESCRIPTION OF THE DRAWINGS

FIG. 3A is a graph showing a Stark shift measured using the method of FIG. 1 for an exemplary voltage sensitive chromophore with a quartz surface and water;

FIG. 3B is a graph showing a Stark shift measured using the method of FIG. 1 for an exemplary voltage sensitive chromophore with a quartz surface and methanol;

FIG. 3C is a graph showing a Stark shift measured using the method of FIG. 1 for an exemplary voltage sensitive chromophore with a quartz surface and acetone;

It is to be understood that the attached drawings are for purposes of illustrating the concepts of the invention and may not be to scale. Identical reference numerals have been used, where possible, to designate identical features that are common to the figures.

DETAILED DESCRIPTION OF THE INVENTION

Figure 1:
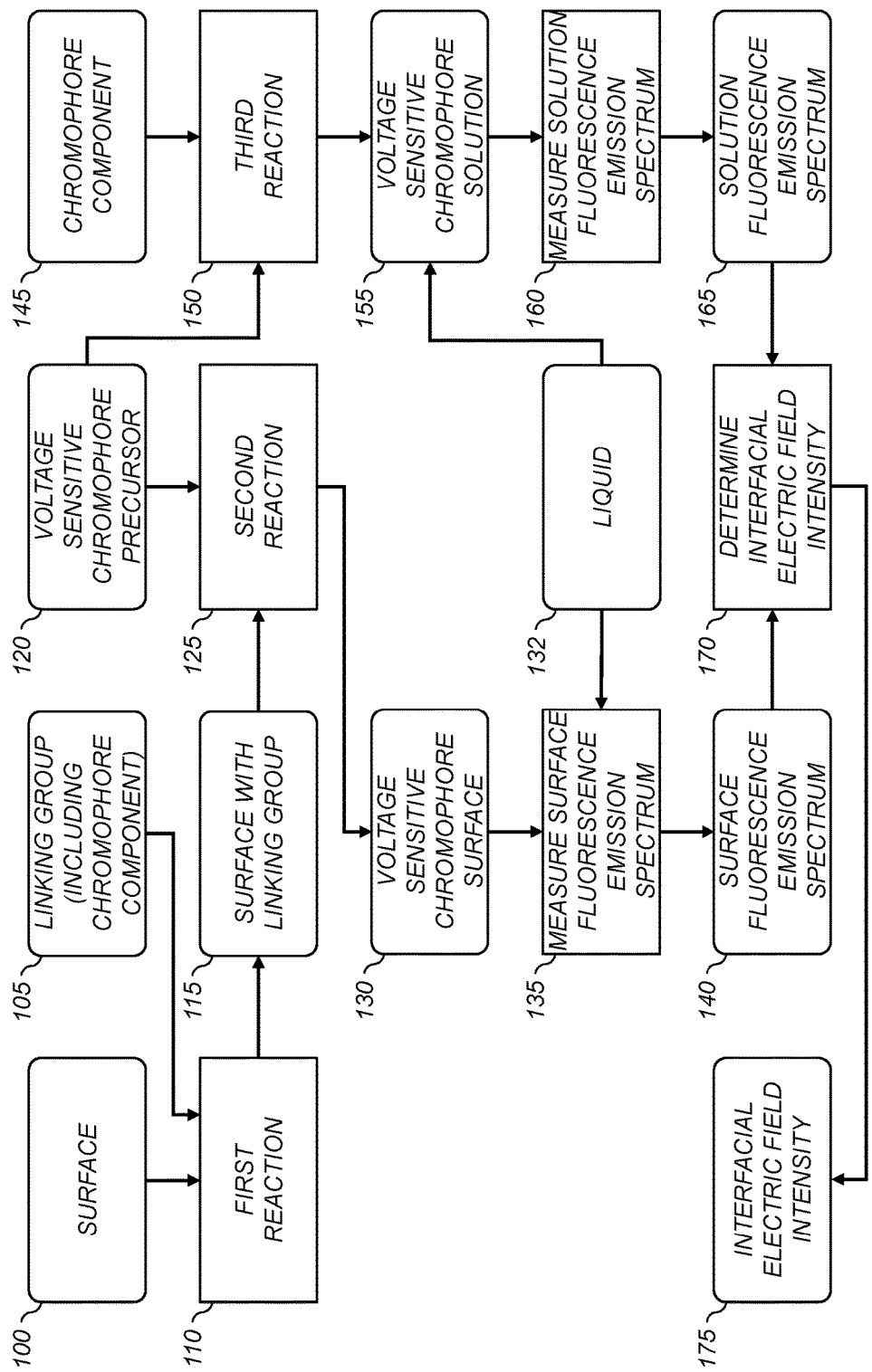
FIG. 1 is a flowchart of a method for measuring an interfacial electric field intensity according to an exemplary embodiment.

The following discussion is directed to various embodiments of the present invention and while some embodiments can be desirable for specific uses, the disclosed embodiments should not be interpreted or otherwise considered to limit the scope of the present invention, as claimed below. In addition, one skilled in the art will understand that the following disclosure has broader application than is explicitly described in the discussion of any embodiment.

The invention is inclusive of combinations of the embodiments described herein. References to "a particular embodiment" and the like refer to features that are present in at least one embodiment of the invention. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular or plural in referring to the "method" or "methods" and the like is not limiting. It should be noted that, unless otherwise explicitly noted or required by context, the word "or" is used in this disclosure in a non-exclusive sense.

Each term that is not explicitly defined in the present application is to be understood to have a meaning that is commonly accepted by those skilled in the art. If the construction of a term would render it meaningless or essentially meaningless in its context, the term definition should be taken from a standard dictionary.

The use of numerical values in the various ranges specified herein, unless otherwise expressly indicated otherwise, are considered to be approximations as though the minimum and maximum values within the stated ranges were both preceded by the word "about". In this manner, slight variations above and below the stated ranges can be used to achieve substantially the same results as the values within the ranges. In addition, the disclosure of these ranges is intended as a continuous range including every value between the minimum and maximum values.

When a solid is immersed in a fluid, an electric field is generated at the interface. This interfacial electric field can also be characterized by a corresponding interfacial potential difference. In accordance with embodiments of the invention, the interfacial electric field (or the corresponding interfacial potential difference) can be quantified by measuring a wavelength shift of the fluorescence emission spectrum between a fast VSD present in the liquid and a monolayer of the VSD affixed to a solid surface in contact with the same liquid (or via a probe with bound VSD immersed in the liquid). Given the same solvent shell structure and reorganization on excitation for bulk and surface VSD bound at the interface, the fluorescence wavelength shift upon excitation is due to the extra energy needed to flip the chromophore dipole in the interfacial electric field. Chromophore dipole moments for a series of voltage sensitive dyes are available in the literature (for example, see P. Fromherz, "Monopole-dipole model for symmetrical solvatochromism of hemicyanine Dyes," J. Phys. Chem., Vol. 99, pp. 7188-7192, 1995). The solvatochromic shift of the VSD is cancelled out since both fluorescence spectra (that is, the bound VSD monolayer and dissolved VSD in the liquid) are recorded in the same solvent.

In various embodiments, the shift in fluorescence emission spectrum of a bound VSD at a solid/liquid interface can be used to perform various functions such as calculating the electric field strength at the interface between a liquid and a surface, identifying or characterizing liquid, determining characteristic differences between a plurality of liquids, and evaluating surface characteristics/uniformity.

FIG. 1 shows a flowchart of a method for determining an interfacial electric field intensity 175 in accordance with an exemplary embodiment. A series of reactions is used to add a monolayer of a voltage sensitive chromophore (i.e., a voltage sensitive dye (VSD)) to a surface 100. The surface 100 can be a non-biological surface such as a silica surface or a polymer surface. In a first reaction 110, a linking group 105 including a chromophore component is covalently attached to the surface 100. The linking group 105 can also be referred to as a "reactive linking molecule." In an exemplary embodiment, the first reaction 110 is performed by: (a) providing a solution including the linking group; (b) providing a surface capable of reacting with the linking group; and (c) bringing the solution into contact with the surface, thereby reacting the linking group with the surface to attach the linking group to the surface with a covalent linkage.

Figure 2A:
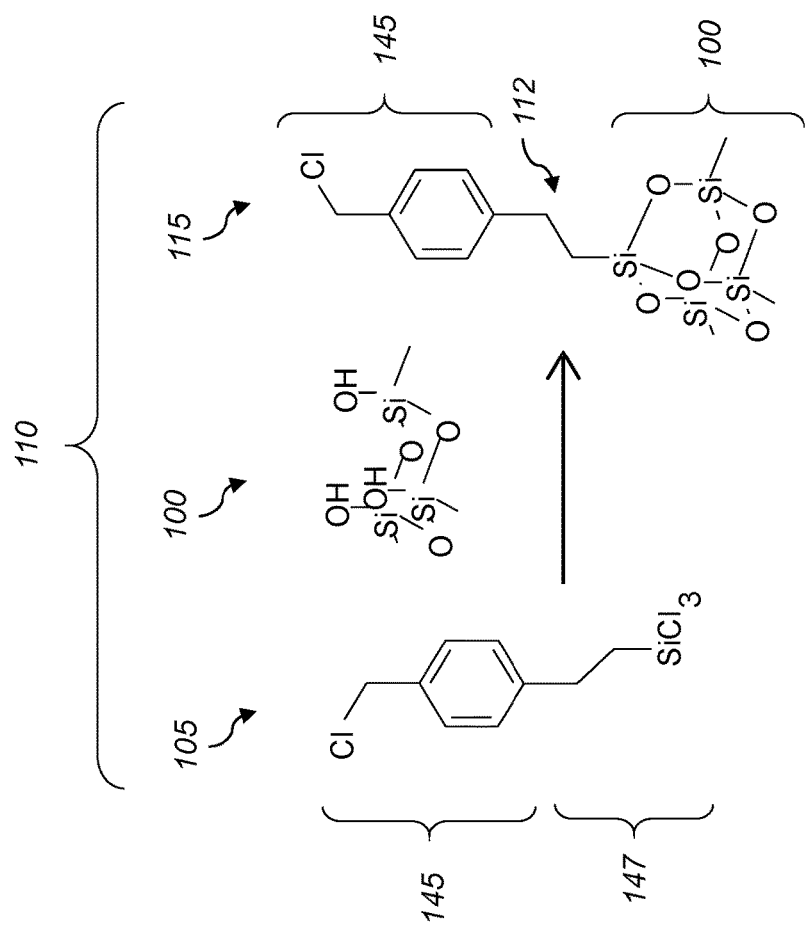
FIG. 2A illustrates an exemplary first reaction useful in the method of FIG. 1.

FIG. 2A illustrates an exemplary first reaction 110 that can be used in accordance with the present invention. In this example, the surface 100 is a silica surface, and the linking group 105 includes a chromophore component 145 and a coupling agent 147. The coupling agent 147 is adapted to couple the linking group 105 to the surface 100. The illustrated chromophore component 145 includes a reactive carbocyclic aromatic linking group (in this case a benzyl halide group), and the coupling agent 147 has a trichlorosilane coupling group. This coupling group is known to couple the silane to a silica surface that has silanol (Si—OH) groups on it, forming Si—O—Si bonds. The resulting surface with linking group 115 includes the chromophore component 145 (i.e., the reactive carbocyclic aromatic linking group) which is attached to the silica surface 100 by a covalent linkage 112.

For other types of surfaces 100, linking groups 105 having other appropriate coupling agents 147 can be used. For example, polymers have carboxylic acid groups (—COOH) that can react with an alcohol (C—OH) coupling group to form an ester (—COOC) linkage. Surfaces with carboxylic acid groups can also couple with an amino (—NH2) coupling group to form an amide (—CONH—) linkage. Alternatively, carboxylic acid groups on surfaces can be coupled to amine coupling groups to form an amino acid linkage. In other examples, isocyanate coupling groups (—NCO) can be used to form a linkage to surfaces with carboxylic acids, alcohols, and amines. Other reactive functional groups include aromatic chloromethyl, amide, hydrazide, aldehyde, hydroxyl, thiol and epoxy. Clearly, similar reactions can be used for many types of surfaces 100, as long as the surfaces 100 have functional groups, or can be modified with functional groups, that will react with the coupling agent 147 that is included in the linking group 105.

Returning to a discussion of FIG. 1, in a second reaction 125, a voltage sensitive chromophore precursor 120 is reacted with the surface with linking group 115 to form a monolayer of the voltage sensitive chromophore that is covalently bound to the surface (i.e., voltage sensitive chromophore surface 130). The voltage sensitive chromophore surface 130 can also be referred to as the "sensor surface" because the monolayer of the voltage sensitive chromophore provides the function of a sensor for sensing properties of the surface, such as the interfacial electric field, or properties of a liquid that is brought into contact with the surface.

Figure 2B:
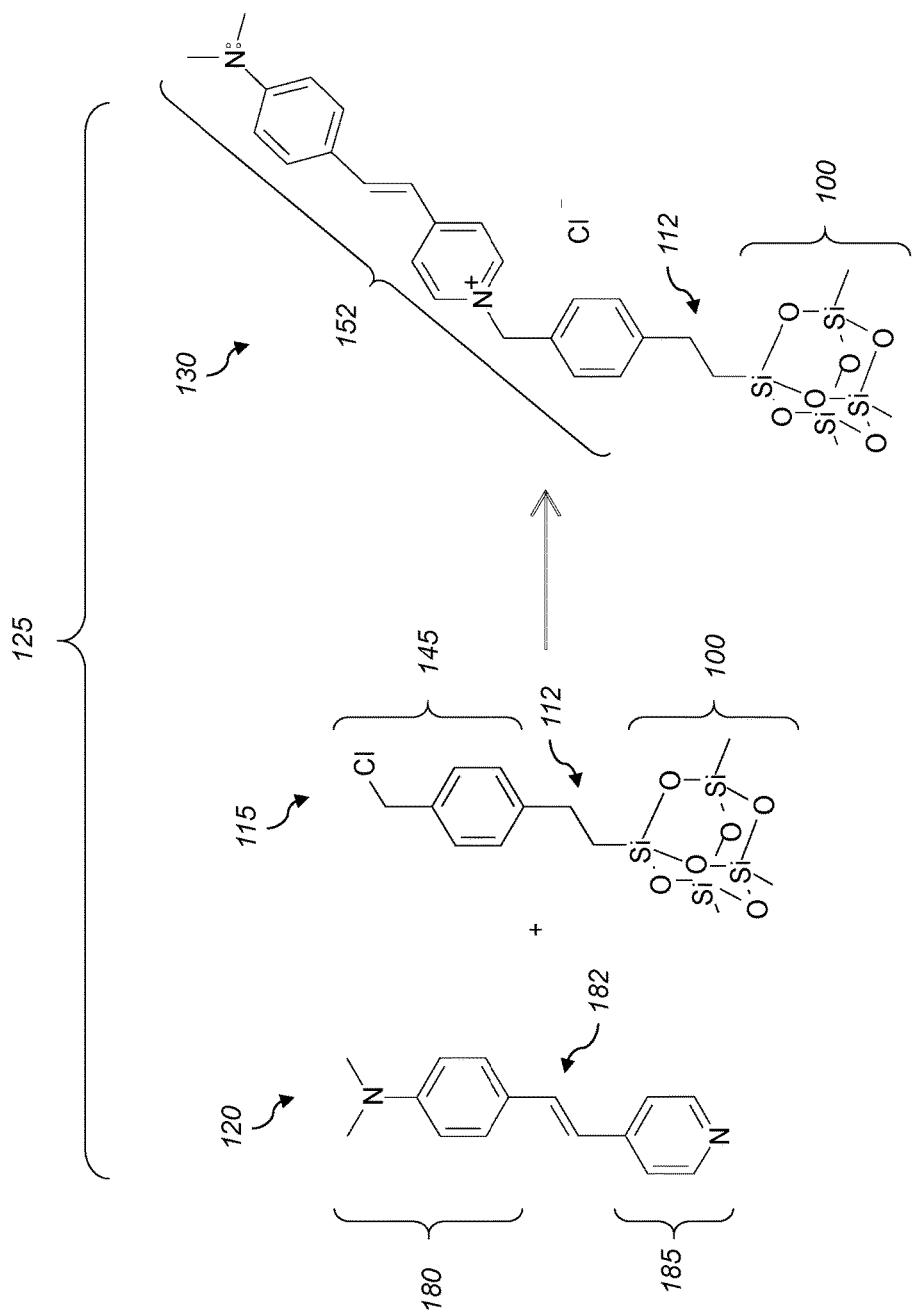
FIG. 2B illustrates an exemplary second reaction useful in the method of FIG. 1.

In an exemplary embodiment, the voltage sensitive chromophore precursor 120 includes a p-substituted dialkylamino aryl group 180 that is linked to a terminal N-containing heterocyclic aromatic group 185 with a conjugate linkage 182 as illustrated in FIG. 2B. In this example, the N-containing heterocyclic aromatic group 185 is a pyridinyl group (a pyridinyl group is a radical derived from pyridine). In the second reaction 125, the chromophore component 145 (i.e., the reactive carbocyclic aromatic linking group) reacts with the terminal N-containing heterocyclic aromatic group 185 of the voltage sensitive chromophore precursor 120 to form the voltage sensitive chromophore 152. The voltage sensitive chromophore 152 can also be referred to as a voltage sensitive dye (VSD). The voltage sensitive chromophore 152 has an associated dipole moment, and is "voltage sensitive" in that its fluorescence emission spectrum (or its absorbance spectrum) changes when it is placed in an electric field, that is, in a region where the voltage (i.e., potential) is changing.

The parts of the voltage sensitive chromophore precursor 120 (i.e., the p-substituted dialkylamino aryl group 180 and the N-containing heterocyclic aromatic group 185) are conjugatively linked and are designed to be reacted with the chromophore component 145 to yield the voltage sensitive chromophore 152. One skilled in the art will recognize that a conjugatively-linked system (also known as a "conjugated system") is a system of bonded atoms including pi orbitals that have been delocalized through bonding. The pi electrons in these orbitals are delocalized over the atoms that participate in the pi orbital bonding. This normally lowers the total energy of the system, and is favored in such bonding as alternating single and double bonds, certain functional groups attached to aromatic rings, alternating single and double bonds attached to aromatic rings, etc.

In alternate embodiments, other types of molecules can be chosen for the two chromophore precursors (i.e., chromophore component 145 and the voltage sensitive chromophore precursor 120), depending on the particular voltage sensitive chromophore that is used (e.g., any of the voltage sensitive chromophores in the aforementioned article by P. Fromherz, entitled "Monopole-dipole model for symmetrical solvatochromism of hemicyanine Dyes"). Typically, the resulting voltage sensitive chromophore is a conjugated system, and is formed from any number of alternating single and double bonds and aromatic rings, including functional groups on the aromatic rings. The requirement is that the precursors are hindered from rotation around internal linkages, so as to maintain the largest dipole moment that reverses upon excitation with actinic light, and that the precursors can be conjugatively linked to form the final chromophore.

The result of the first and second reactions 110, 125 is to provide a monolayer of the voltage sensitive chromophore that is covalently bound to the surface 100 (i.e., the voltage sensitive chromophore surface 130). In accordance with the method of FIG. 1, a third reaction 150 is also performed to form a voltage sensitive chromophore 152 (FIG. 2C), which is dissolved in a liquid 132 to provide a voltage sensitive chromophore solution 155.

Figure 2C:
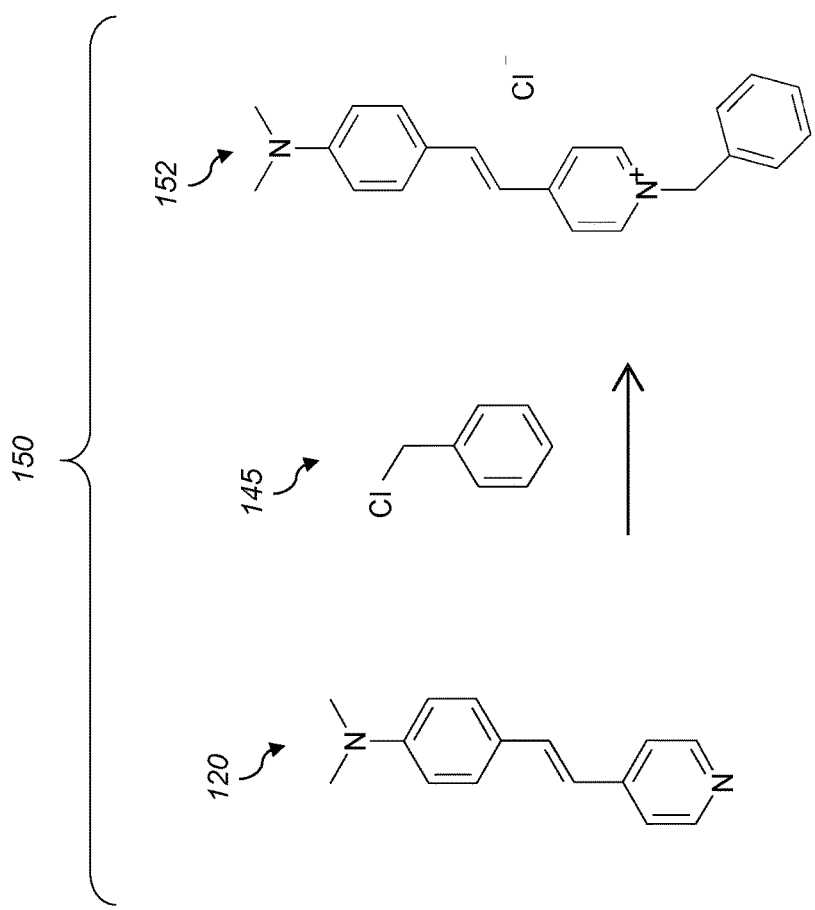
FIG. 2C illustrates an exemplary third reaction useful in the method of FIG. 1.

As illustrated in FIG. 2C, in an exemplary embodiment the third reaction 150 is performed by reacting the voltage sensitive chromophore precursor 120 with chromophore component 145 (which is the same chromophore component 145 that was included in the linking group 105 (see FIG. 2A)), thereby forming the voltage sensitive chromophore 152. The voltage sensitive chromophore 152 is dissolved in a sample of the liquid 132, to provide the voltage sensitive chromophore solution 155. In some cases, the third reaction 150 is carried out in the liquid 132 to directly provide the voltage sensitive chromophore solution 155. In other cases, the third reaction 150 can be carried out in another solvent, and the voltage sensitive chromophore 152 can then be dried and re-dissolved in the liquid 132 to provide the voltage sensitive chromophore solution 155. Examples of appropriate liquids 132 that can be used would include water, methanol, ethanol, chloroform, acetone, toluene and methyl chloride. In general, any liquid that does not react chemically with the voltage sensitive chromophore surface 130 to break the covalent bond between the voltage sensitive chromophore 152 and the surface 100 and does not change the conjugated pi system of the voltage sensitive chromophore 152 can be used in accordance with the present invention. For the method of FIG. 1, another requirement is that the voltage sensitive chromophore 152 be soluble in the liquid 132.

After, the voltage sensitive chromophore surface 130 and the voltage sensitive chromophore solution 155 have been prepared, fluorescence emission spectra are measured and compared. A measure surface fluorescence emission spectrum step 135 is used to measure a surface fluorescence emission spectrum 140 of the voltage sensitive chromophore surface 130 while it is in contact with a sample of the liquid 132. This involves irradiating the voltage sensitive chromophore surface 130 with actinic radiation provided by an irradiation source while it is in contact with the liquid and using a fluorescence sensing system to measure the emission spectrum of the resulting fluorescent radiation. In this context, "actinic radiation" is radiation that is adapted to stimulate fluorescence of the voltage sensitive chromophore. Typically, the actinic radiation for many voltage sensitive chromophores will be ultraviolet (UV) radiation or short wavelength visible radiation. For example, in the case of the exemplary voltage sensitive chromophore 152 of FIGS. 2B-2C, the actinic radiation can be radiation having a wavelength of 480 nm. In some configurations, the liquid 132 can be brought into contact with the voltage sensitive chromophore surface 130 by using a fluid cell (e.g., a cuvette), where the voltage sensitive chromophore surface 130 is used for one or more surfaces of the fluid cell. Similarly, a measure solution fluorescence emission spectrum step 160 is used to measure a solution fluorescence emission spectrum 165 of the voltage sensitive chromophore solution 155. This can be accomplished by using a fluid cell having transparent windows filled with the voltage sensitive chromophore solution 155.

In some configurations, the solution fluorescence emission spectrum 165 can be predetermined and stored for later comparison with the surface fluorescence emission spectrum 140. For example, a number of different surfaces 100 can be evaluated using the method of FIG. 1. Voltage sensitive chromophore surfaces 130 can be prepared, each having a monolayer of the voltage sensitive chromophore. Surface fluorescence emission spectrum 140 can then be measured for each of the surfaces 100, and can be compared to the stored solution fluorescence emission spectrum 165 for the voltage sensitive chromophore solution 155 rather than repeating the measurement of the solution fluorescence emission spectrum 165.

Once the surface fluorescence emission spectrum 140 and the solution fluorescence emission spectrum 165 are determined, they are compared using a determine interfacial electric field intensity step 170 to determine a measured interfacial electric field intensity 175. As will be discussed below, in an exemplary arrangement, the interfacial electric field intensity 175 is determined responsive to a Stark shift in the peaks of the fluorescence emission spectra.

FIG. 3A shows a graph 300 comparing measured fluorescence emission spectra for the case where the exemplary voltage sensitive chromophore 152 of FIGS. 2B-2C is used with a quartz surface 100, and the liquid 132 (FIG. 1) is water. The fluorescence emission spectra were measured using a Spex-JY-Horiba Tau 3 spectrometer with a double monochromator on both the excitation and emission side, and a Peltier-cooled photomultiplier tube detector. To measure the surface fluorescence emission spectrum 140, a quartz cell (i.e., a cuvette) having a monolayer of the voltage sensitive chromophore 152 on the inside surface was prepared by performing the first and second reactions 110, 125 in the cuvette. The cuvette was dried, and then filled with the liquid 132 and irradiated normal to the surface 100 with actinic radiation having an excitation wavelength of 480 nm, and the resulting emission spectrum was measured at an angle of 22°. To measure the solution fluorescence emission spectrum 165, the voltage sensitive chromophore solution 155 was prepared by dissolving 1 mg of the voltage sensitive chromophore 152 in 15 g of water. This solution was diluted by adding 1 ml of the solution to 19 ml of water (a 1/20 dilution). A cuvette was then filled with the voltage sensitive chromophore solution 155, and the solution fluorescence emission spectrum 165 was measured as before using the same excitation wavelength (480 nm).

It can be seen that the surface fluorescence emission spectrum 140 measured for the voltage sensitive chromophore surface 130 (FIG. 1) having a monolayer of the voltage sensitive chromophore 152 has been shifted toward a higher wavenumber (i.e., to a higher energy level) relative to the solution fluorescence emission spectrum 165 measured for the voltage sensitive chromophore solution 155 (FIG. 1). In this case, the Stark shift between the fluorescence emission spectra (i.e., the change in the wave number between the spectral peeks) was determined to be $\Delta\tilde{v}=260$ $cm^{-1}$.

FIG. 3B shows an analogous graph 310 comparing measured fluorescence emission spectra for the case where the liquid is methanol. In this case, the shift between the fluorescence emission spectra was determined to be $\Delta\tilde{v}=482$ $cm^{-1}$. Similarly, FIG. 3C shows a graph 320 comparing measured fluorescence emission spectra for the case where the liquid is acetone. In this case, the shift between the fluorescence emission spectra was determined to be $\Delta\tilde{v}=687$ $cm^{-1}$.

Those skilled in the art will recognize that it will typically be desirable to smooth the measured fluorescence emission spectra using an appropriate smoothing algorithm to smooth out any measurement noise. Any appropriate curve smoothing algorithm known in the art can be used in accordance with the present invention. Example curve smoothing algorithms would include low-pass filter algorithms, smoothing spline algorithms, and curve-fitting algorithms that fit a standard functional form (e.g., a Gaussian function) to the measured data. A peak-finding algorithm can then be used to identify the peaks of the fluorescence emission spectra in order to determine the Stark shift. Peak-finding algorithms are well-known in the data processing art, and any appropriate algorithm can be used in accordance with the present invention.

Figure 4:
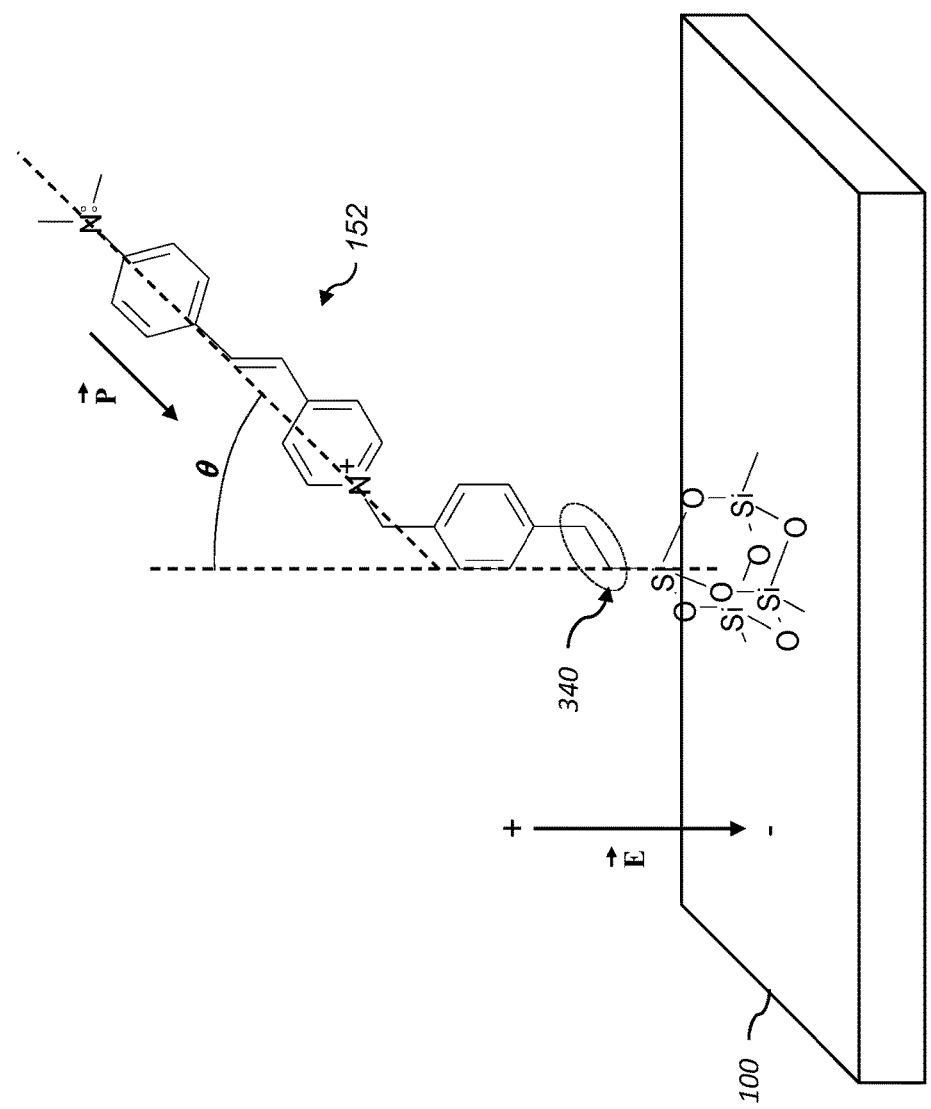
FIG. 4 is a schematic showing a voltage sensitive chromophore bonded to a silica surface.

FIG. 4 is a schematic showing a molecule of the voltage sensitive dye 152 bonded to a silica surface 100. The voltage sensitive chromophore 152 has an associated dipole moment $\vec{P}$ and the surface 100 has an associated interfacial electric field $\vec{E}$, with θ being the angle between the $\vec{P}$ and $\vec{E}$ vectors. The voltage sensitive dye 152 can rotate around transperiplanar rotomer 340 to align with the $\vec{E}$ field.

Figure 5B:
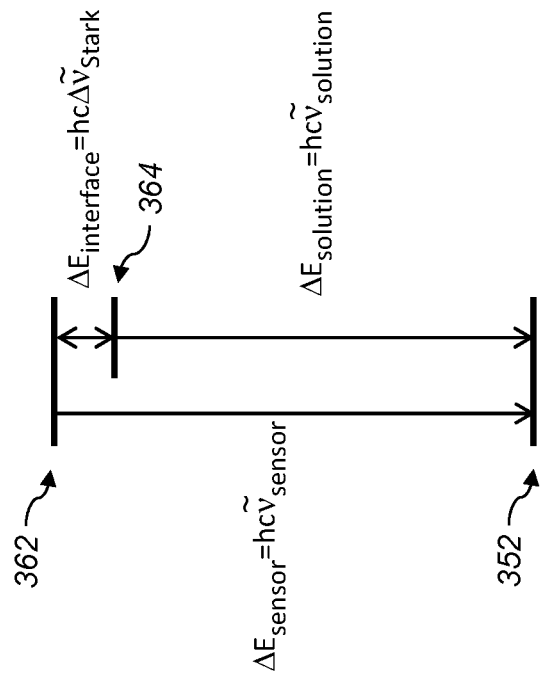
FIG. 5B is an energy diagram illustrating the energy difference resulting from an interfacial electric field.
Figure 5A:
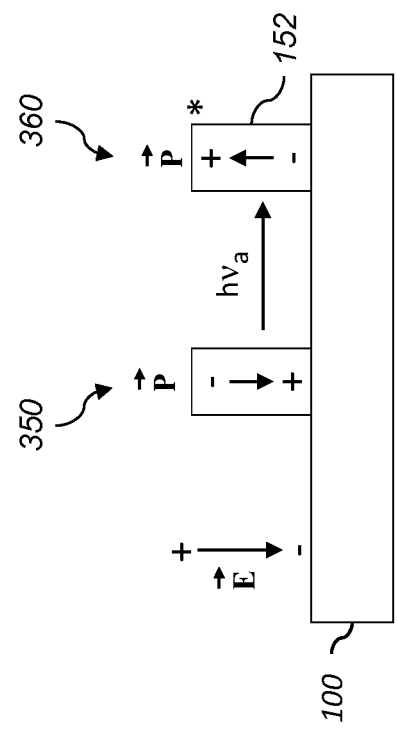
FIG. 5A is a schematic showing a monolayer of voltage sensitive chromophore where the dipole P is flipped upon excitation with actinic radiation in the presence of an interfacial electric field.

FIG. 5A is a schematic showing a monolayer of the voltage sensitive chromophore 152 having an associated dipole moment $\vec{P}$ bound to surface 100 in the presence of an interfacial electric field $\vec{E}$. Upon illumination by actinic radiation ($hv_a$), there is a displacement of charge within the voltage sensitive chromophore 152, causing the dipole moment $\vec{P}$ to be flipped from ground state 350 to exited state 360.

FIG. 5B is an energy diagram showing the ground state energy level 352 associated with the ground state 350 (FIG. 5A) and the excited state energy level 362 associated with the excited state 360 (FIG. 5A). As the voltage sensitive chromophore 152 falls from the exited state 360 back to the ground state 350, a photon is emitted having an energy $\Delta E_{sensor}$ given by:

$$\Delta E_{sensor} = hc\tilde{v}_{sensor} \tag{1}$$

where $h=6.626\times10^{-34}$ J·s is Planck's constant, $c=3.00\times10^8$ m/s is the speed of light, and $\tilde{v}_{sensor}$ is the wave number (1/wavelength) of the emitted photon.

The excited state energy level 364 associated with the voltage sensitive chromophore 152 when it is in solution is lower than the excited state energy level 362 for the sensor where the voltage sensitive chromophore 152 is bound to the surface 100, such that the emitted photons have a lower energy $\Delta E_{solution}$ given by:

$$\Delta E_{solution} = hc\tilde{v}_{solution} \quad (2)$$

where $\tilde{v}_{solution}$ is the wave number of the emitted photon.

The difference between the energies of the excited state energy levels 362, 364 ($\Delta E_{interface}$) corresponds to the Stark shift:

$$\Delta E_{interface} = \Delta E_{sensor} - \Delta E_{solution} \quad (3)$$
$$= hc\tilde{v}_{sensor} - hc\tilde{v}_{solution}$$
$$= hc\Delta\tilde{v}_{Stark}$$

where the Stark shift $\Delta\tilde{v}_{Stark} = \tilde{v}_{sensor} - \tilde{v}_{solution}$ is the difference between the wave numbers of the emitted photons in the sensor and solution configurations. The Stark shift can also be related to a corresponding difference in the wavelengths:

$$\Delta\tilde{v}_{Stark} = \tilde{v}_{sensor} - \tilde{v}_{solution} \quad (4)$$
$$= 1/\lambda_{sensor} - 1/\lambda_{solution}$$
$$= (\lambda_{solution} - \lambda_{sensor})/(\lambda_{sensor} \cdot \lambda_{solution})$$

where $\lambda_{sensor}$ and $\lambda_{solution}$ are the wavelengths of the emitted photons in the sensor and solution configurations, respectively.

The energy difference $\Delta E_{interface}$ corresponds to the energy difference between the two orientations of the chromophore dipole in the presence of the interfacial electric field, which is directly related to the magnitude of interfacial electric field $\vec{E}$ and the chromophore dipole moment $\vec{P}$, and the angle $\theta$ between them:

$$\Delta E_{interface} = 2|\vec{E}||\vec{P}|\cos\theta \quad (5)$$

Combining Eqs. (3) and (5) and solving for the magnitude of the interfacial electric field $\vec{E}$ gives:

$$|\vec{E}| = \frac{hc\Delta\tilde{v}_{Stark}}{2|\vec{P}|\cos\theta} \quad (6)$$

Therefore, experimentally measuring the Stark shift $\Delta\tilde{v}_{Stark}$ enables the magnitude of the interfacial electric field $|\vec{E}|$ to be determined given estimates of the dipole moment and the angle that the chromophore dipole makes with the interfacial electric field at the interface. The cosine function is relatively close to 1.0 for a fairly large range of angles around $\theta=0°$, so that it can be neglected in many cases without significantly impacting the calculated result. Even if $\theta$ is as large as 60°, the calculation of the electric field would only be in error by a factor of about 2×. Note that any solvatochromic shift associated with the particular liquid is nulled out given that both spectra are taken in the same liquid.

The dipole moment of the voltage sensitive chromophore 152 of FIGS. 2B-2C, which was used to produce the experimental results of FIGS. 3A-3C was estimated to be:

$$\vec{P} = e \cdot \delta/2 = (1.60 \times 10^{-19}\text{C})(0.217\text{ nm})/2 = 1.74 \times 10^{-29} \text{C} \cdot \text{m} \quad (7)$$

where $e=1.60\times10^{-19}$ C is the elementary charge, and $\delta=0.217$ nm is the estimated distance that the charge is displaced when the polarity of the dipole is flipped. Using this value, the magnitudes of the interfacial electric fields for each case can be calculated using Eq. (6). The results are summarized in Table 1, where the dipole angle was estimated to be $\theta=45°$.

TABLE 1

Measured interfacial electric fields

| Surface | Liquid | $\Delta\tilde{v}$ (cm$^{-1}$) | $|\vec{E}|$ (V/cm) |
|---|---|---|---|
| quartz | water | 260 | $2.11 \times 10^6$ |
| quartz | methanol | 482 | $3.90 \times 10^6$ |
| quartz | acetone | 687 | $5.56 \times 10^6$ |

Figure 6:
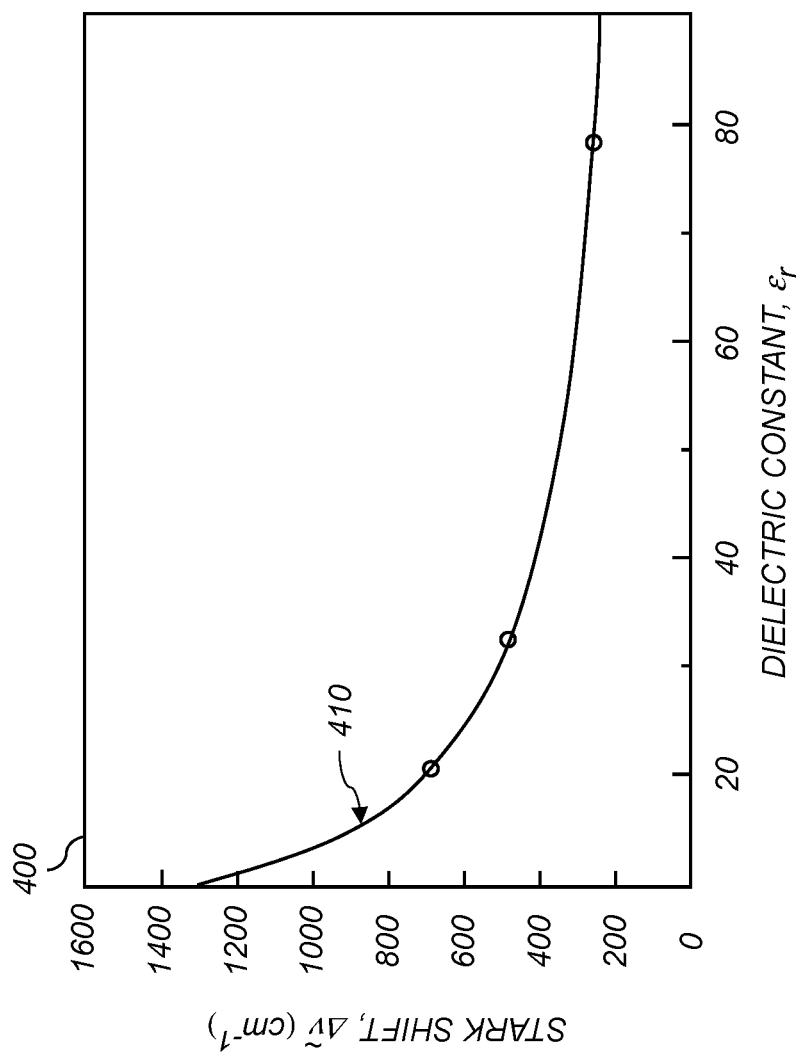
FIG. 6 is a graph illustrating a relationship between the dielectric constant of the liquid and the resulting Stark shift.

From Table 1, it can be seen that for a given surface (e.g., quartz with a monolayer of a particular voltage sensitive chromophore 152), the magnitude of the interfacial electric field, and therefore the Stark shift, vary according to the characteristics of the liquid. In some embodiments this fact can be used to provide a sensor for determining characteristics of an unknown liquid. One of the primary liquid characteristics that will influence the interfacial electric field is the dielectric constant of the liquid. FIG. 6 shows a graph 400 of the Stark shift $\Delta\tilde{v}_{Stark}$ as a function of the dielectric constant, $\varepsilon_r$, using the data from Table 1. A curve 410 has been fit to the measured data, giving a relationship between the dielectric constant and the resulting Stark shift. If the Stark shift is measured for an unknown liquid, the curve 410 can be used to determine an estimate of the dielectric constant of the liquid.

Figure 7:
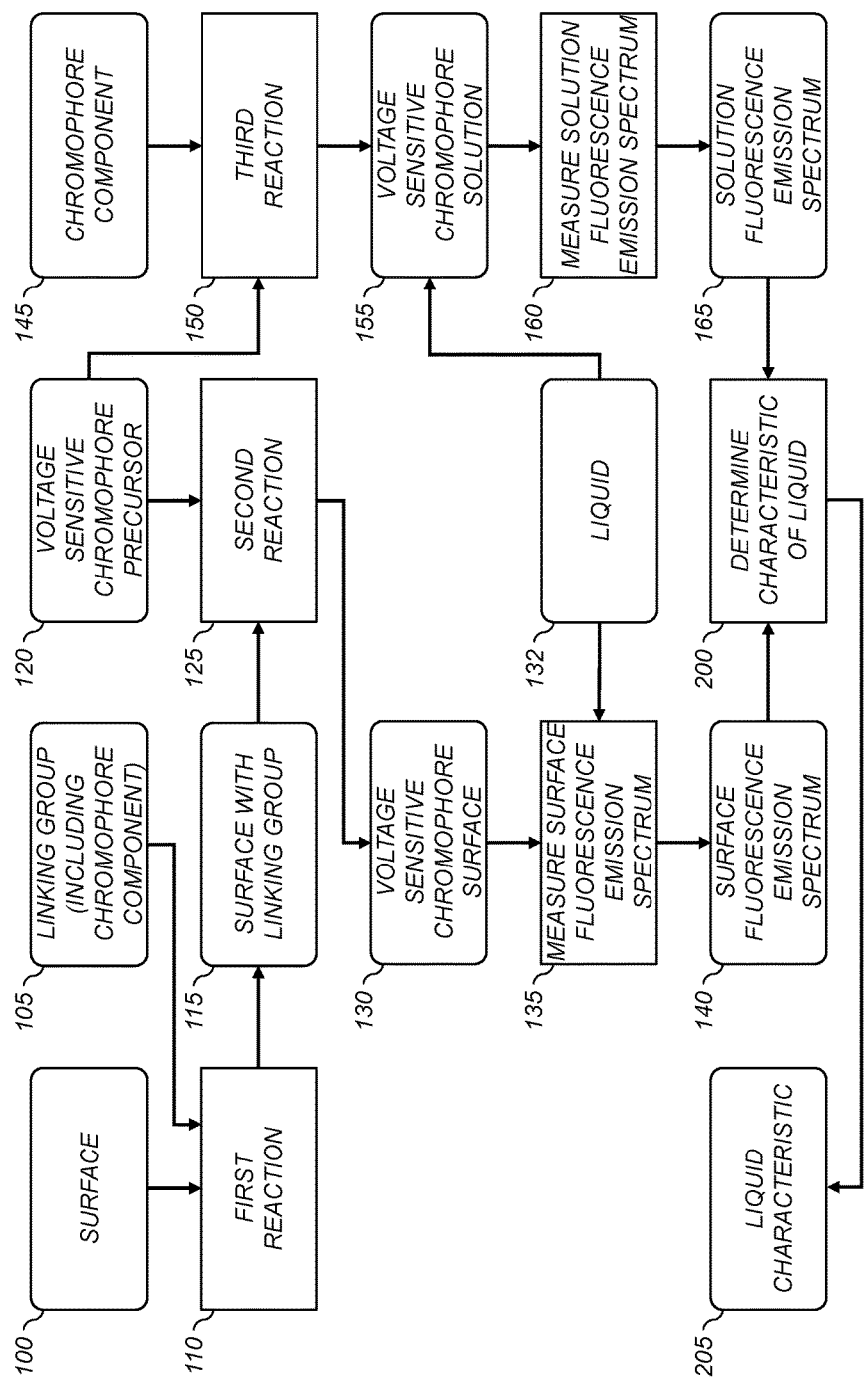
FIG. 7 is a flowchart of a method for measuring a liquid characteristic according to an exemplary embodiment.

FIG. 7 shows a flow chart of a method for determining a characteristic of a liquid in accordance with an embodiment of the invention. The method of FIG. 7 is identical to that of FIG. 1, except that rather than analyzing the surface and solution fluorescence emission spectra 140, 165 to determine the interfacial electric field intensity 175, a determine characteristic of liquid step 200 is used to determine a liquid characteristic 205.

In an exemplary arrangement, the determine characteristic of liquid step 200 computes the Stark shift, and then uses the curve of FIG. 6 to determine a dielectric constant of the liquid 132. For the case where the liquid 132 is an unknown substance, the determine characteristic of liquid step 200 can be used to identify the liquid, or to determine one or more candidate identities for the liquid. For example, a table of dielectric constants for known liquids can be prepared, and the measured dielectric constant for the unknown liquid can be compared to the table to identify candidate liquids having dielectric constants that match the measured dielectric constant to within the associated measurement error. This approach can be used to construct sensors capable of identifying or characterizing liquids without the use of complexing agents or selective membranes as is generally required in the prior art. Other examples of liquid characteristics 205 that could be determined in a similar fashion in accordance with the invention would include the polarizability and electric susceptibility.

In some embodiments, the determine characteristic of liquid step 200 determines the liquid characteristic 205 based on only the surface fluorescence emission spectrum 140, without measuring the solution fluorescence emission spectrum 165. For example, surface fluorescence emission spectra 140 can be measured for a library of common liquids using the voltage sensitive chromophore surface 130. A surface fluorescence emission spectrum 140 can then be measured for an unknown liquid 132. The resulting surface fluorescence emission spectrum 140 for the unknown liquid can then be compared to the library of surface fluorescence emission spectra 140 for the common liquids to determine whether there is a match. If so, it can be determined that the unknown liquid is likely to be the matching liquid from the library. In this example, the determined characteristic 205 is the identity of the liquid 132.

Figure 8:
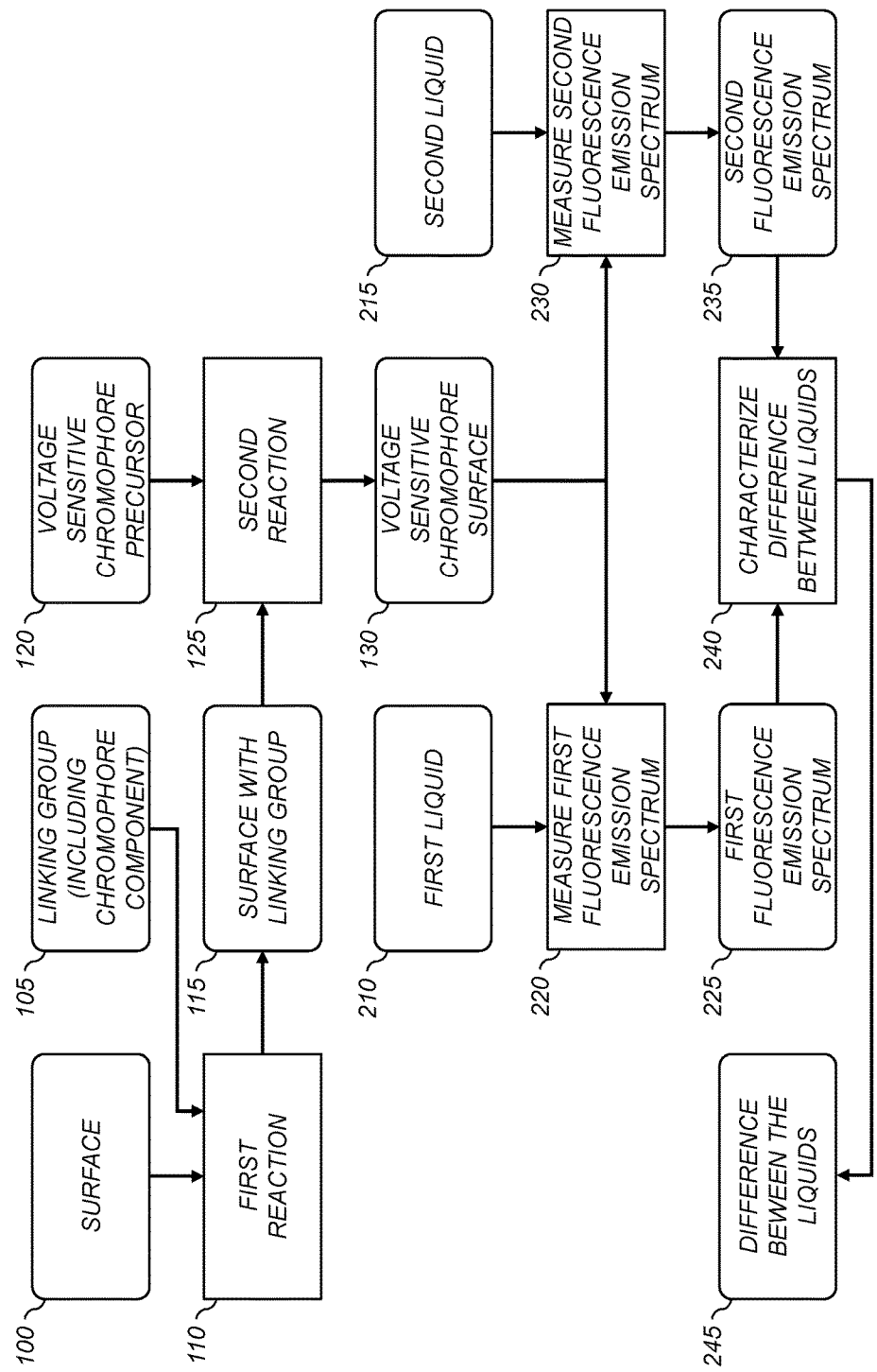
FIG. 8 is a flowchart of a method for determining characteristic differences between two liquids according to an exemplary embodiment.

FIG. 8 shows a flow chart of a method for determining a characteristic difference between different liquids in accordance with an embodiment of the invention. The method of FIG. 8 is similar to that of FIG. 1, except that rather than comparing the fluorescence emission spectrum determined from the voltage sensitive chromophore surface 130 with that measured for the voltage sensitive chromophore solution 155, the voltage sensitive chromophore surface 130 is used to compare a first liquid 210 and a second liquid 215. In this case, a measure first fluorescence emission spectrum step 220 provides a first fluorescence emission spectrum 225 for the first liquid 210 in contact with voltage sensitive chromophore surface 130, and a measure second fluorescence emission spectrum step 230 provides a second fluorescence emission spectrum 235 for the second liquid 215 in contact with the voltage sensitive chromophore surface 130. A characterize difference between liquids step 240 is then used to compare the first and second fluorescence emission spectra 225, 235 to determine a difference between the liquids 245. For example, the difference between the liquids 245 can be a parameter representing the degree of similarity (or difference) between the first and second fluorescence emission spectra 225, 235 (e.g., a correlation coefficient, or an RMS difference between the spectra). Alternatively, the difference between the liquids 245 can be a parameter indicating the likelihood that the first liquid 210 and the second liquid 215 are the same (e.g., a statistical confidence level). In other arrangements, the difference between the liquids 245 can be one or more parameters characterizing the difference between the first and second fluorescence emission spectra 225, 235 (e.g., a difference between the peak wavelengths, or a difference function representing the difference as a function of wavelength).

A variety of applications can be envisioned for the method of FIG. 8. For example, a distillation process can be used to extract a particular liquid from a mixture of liquids. During the distillation process, the purity of the liquid will gradually increase. In this case, the first liquid 210 can be a reference sample of liquid having a desired level of purity, and the second liquid 215 can be a sample of the distillation product at a particular point in time. The difference between the liquids 245 can be determined at a series of times, and the distillation process can be terminated when it is determined that the difference between the liquids 245 falls below a predefined threshold indicating that the distillation product matches the reference sample.

While the method of FIG. 8 was described with respect to comparing first and second liquids 210, 215, one skilled in the art will recognize that the method can be generalized to compare two fluids, where one or both of the fluids can be gases.

The determine interfacial electric field intensity step 170 of FIG. 1, the determine characteristic of liquid step 200 of FIG. 7 and the characterize difference between liquids step 240 of FIG. 8 generally involve making a comparison between a pair of fluorescence emission spectra. The comparison methods described above have involved determining a Stark shift by comparing the positions of the peaks of the fluorescence emission spectra (either in terms of wave number differences or wavelength differences). In other arrangements, different methods can be used to compare the two fluorescence emission spectra. For example, in one variation, rather than comparing the peaks of the fluorescence emission spectra, centroids (or other central tendency metrics) can be determined for each fluorescence emission spectra and compared. Other statistical metrics can also be used to characterize the fluorescence emission spectra, including standard deviation, skew and kurtosis.

Figure 9:
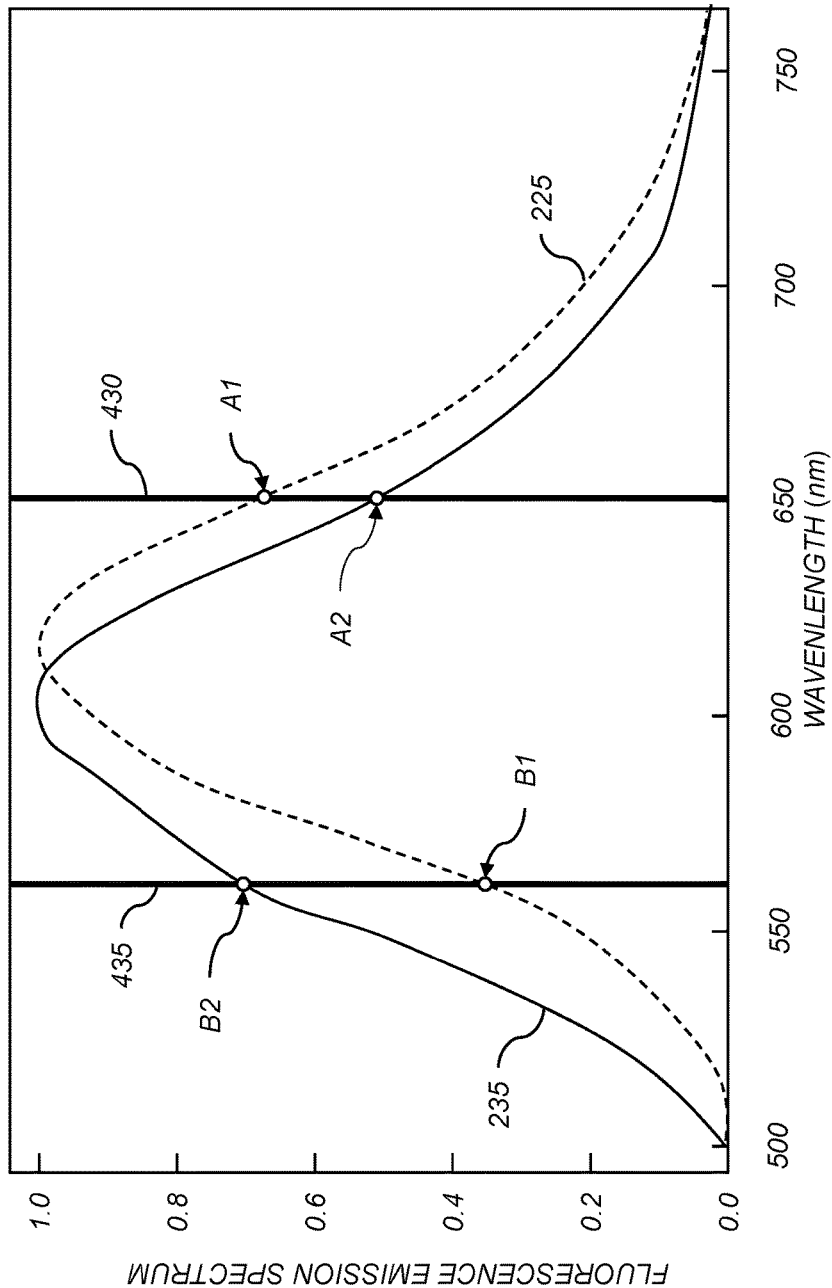
FIG. 9 is a graph illustrating a method for comparing two fluorescence emission spectra at first and second wavelengths.

FIG. 9 is a graph illustrating exemplary first and second fluorescence emission spectra 225, 235. In this case, the first surface fluorescence emission spectrum 225 was determined for a first liquid 210 (water), and the second fluorescence emission spectrum 225 was determined for a second liquid 215 (methanol), in accordance with the method of FIG. 8.

In an exemplary class of spectrum comparison methods, a first wavelength 430 and a second wavelength 435 are defined. In the illustrated example, the first wavelength 430 is 650 nm and the second wavelength 435 is 560 nm. Preferably, the first and second fluorescence emission spectra 225, 235 overlap with both the first and second wavelengths 430, 435. A first intensity ratio R1=A1/B1 is determined for the first fluorescence emission spectrum 225, where A1 is the value of the first fluorescence emission spectrum 225 at the first wavelength 430, and B1 is the value of the first fluorescence emission spectrum 225 at the second wavelength 435. Likewise, a second intensity ratio R2=A2/B2 is determined for the second fluorescence emission spectrum 235, where A2 is the value of the second fluorescence emission spectrum 235 at the first wavelength 430, and B2 is the value of the second fluorescence emission spectrum 235 at the second wavelength 435.

If a fluorescence emission spectrum is centered between the first and second wavelengths 430, 435, then the intensity ratio will be approximately equal to 1.0. If the spectrum is to the left of center, then the intensity ratio will be smaller than 1.0, and if the spectrum is to the right of center, then the intensity ratio will be greater than 1.0. Therefore, the intensity ratio will be a measure of the location of the spectral peak for the spectrum, and the difference in the intensity ratios will be a measure of the shift in the spectral peaks.

Table 2 shows exemplary ratios determined for the fluorescence emission spectra of FIG. 9. It can be seen that the difference between spectral peaks is clearly reflected by differences in the intensity ratios. The larger intensity ratio for water reflects the fact that its emission spectrum (first fluorescence emission spectrum 225) is shifted to the right relative to that for methanol (second fluorescence emission spectrum 235).

TABLE 2

| | Intensity ratio comparison | | |
|---|---|---|---|
| | A ($\lambda$ = 650 nm) | B ($\lambda$ = 560 nm) | R = A/B |
| Water | 0.680 | 0.349 | 1.95 |
| Methanol | 0.510 | 0.690 | 0.74 |

In some embodiments, the intensity ratios can be related to the quantity being measured (e.g., the interfacial electric field intensity 175 (FIG. 1) or the liquid characteristic 205 (FIG. 7)) by evaluating the intensity ratios for a set of reference configurations and fitting a function to the results.

In other types of spectrum comparison methods more than two wavelengths can be compared. For example, additional spectra ratios can be computed between additional wavelengths pairs to provide additional information about the shape and position of the spectrum. In some cases, a spectral difference can be determined by subtracting the two spectra on a wavelength-by-wavelength basis. The spectral difference can then be analyzed to characterize the difference between the spectra. For example, an RMS spectral difference can be computed between the spectra measured for two liquids to determine if the spectra are statistically indistinguishable, indicating that the two liquids may be the same. In some configurations, the spectra can be analyzed to determine corresponding color values (e.g., in the well-known L*a*b* color space), and color differences can be computed (e.g., ΔE* values) to characterize the difference between two spectra.

In some embodiments, many spectra are compared to determine which liquid is present at the surface. In such cases, any classification and discrimination analysis methods known in the statistics and chemometrics fields can be used. These methods include the use of the Mahalanobis distance, K nearest neighbor, discriminant analysis, cluster analysis, factor analysis, and principal component analysis (PCA) and obtaining spectral contrast angles between pairs of spectra. As the number of compared spectra increases, the more useful these methods become, especially PCA and cluster analysis, leading to full pattern recognition of the spectral shape of a given liquid/chromophore spectral response. Many of these techniques can be extended to spectral modeling or deconvolution, allowing a liquid to be identified by all of its wavelength responses.

Figure 10:
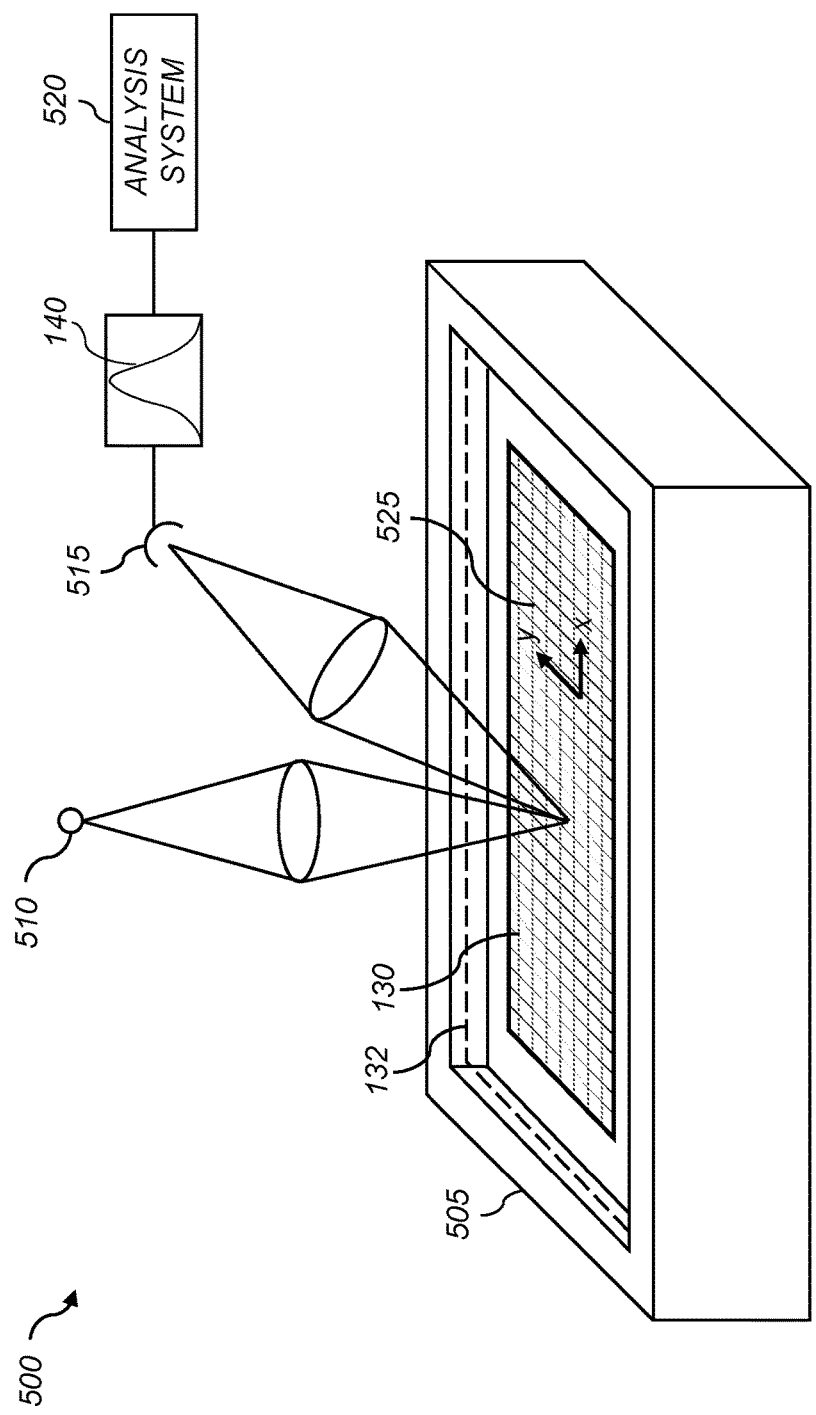
FIG. 10 illustrates an exemplary surface evaluation system for evaluating a surface in accordance with an exemplary embodiment.

FIG. 10 shows an exemplary surface evaluation system 500 for evaluating a surface. A chromophore application system (not shown) is used to apply a monolayer of a voltage sensitive chromophore 152 (FIG. 2B) to a surface 100 (FIG. 2B) to provide voltage sensitive chromophore surface 130. The applied voltage sensitive chromophore 152 is covalently bound to the surface 100 and has a fluorescence emission spectrum which varies in accordance with a characteristic of the surface 100 (e.g., the interfacial electric field). The voltage sensitive chromophore surface 130 is mounted in a surface holder 505 for measurement. One skilled in the art will recognize that a wide variety of arrangements can be used for the surface holder 505 in accordance with the present invention. In the illustrated configuration, the surface holder 505 includes a recessed surface that is adapted to receive a liquid 132 in some embodiments. In other configurations, the voltage sensitive chromophore surface 130 can be a surface of a liquid cell (e.g., a cuvette), and the surface holder 505 can be a mechanism for holding the liquid cell.

An irradiation source 510 is positioned to irradiate the voltage sensitive chromophore surface 130 with actinic radiation that stimulates fluorescence of the voltage sensitive chromophore 152. A fluorescence sensing system 515 (e.g., a spectrophotometer) measures a surface fluorescence emission spectrum 140 which is emitted by the irradiated voltage sensitive chromophore surface 130. In some embodiments, the fluorescence sensing system 515 is a micro-spectrophotometer which is adapted to sense the surface fluorescence emission spectrum 140 emitted from a localized area voltage sensitive chromophore surface 130. In this case, the irradiation source 510 can illuminate the same localized area (as shown in FIG. 10), or alternatively can illuminate a broad area of the voltage sensitive chromophore surface 130.

Generally, the surface fluorescence emission spectrum 140 will be measured while the voltage sensitive chromophore surface 130 is in contact with some fluid (e.g., a liquid or a gas). In some embodiments, the surface fluorescence emission spectrum 140 can be measured while the voltage sensitive chromophore surface 130 is exposed to air (or some other gas). In other embodiments, the surface fluorescence emission spectrum 140 can be measured while the voltage sensitive chromophore surface 130 is in contact with a liquid 132. In this case, a liquid applicator (not shown) can be used to bring the liquid 132 into contact with the voltage sensitive chromophore surface 130. For example, the liquid 130 can be added into the recessed region in the surface holder 505 of FIG. 10. For the case where the voltage sensitive chromophore surface 130 is the wall of a liquid cell, the liquid applicator can add the liquid 132 to the liquid cell. Depending on the geometry of the voltage sensitive chromophore surface 130 and the other components of the surface evaluation system 500, one skilled in the art will recognize that a wide variety of liquid applicators can be used to bring the liquid 132 into contact with the voltage sensitive chromophore surface 130.

An analysis system 520 is used to analyze the surface fluorescence emission spectrum 140 to evaluate a characteristic of the voltage sensitive chromophore surface 130. In an exemplary embodiment, the characteristic is the interfacial electric field intensity 175 (FIG. 1) of the voltage sensitive chromophore surface 130. The analysis steps involved with the determination of the interfacial electric field intensity 175 have been discussed above. In some embodiments, the solution fluorescence emission spectrum 165 of the voltage sensitive chromophore solution 155 can be predetermined and stored as a reference fluorescence emission spectrum for comparison with the measured surface fluorescence emission spectrum 140 at a later time. In other embodiments, the analysis system 520 can be used to determine a liquid characteristic 205 as discussed with respect to FIG. 7, or to determine differences between a plurality of liquids, as was discussed with respect to FIG. 8.

In some embodiments, the fluorescence sensing system 515 measures a plurality of surface fluorescence emission spectra 140 at a lattice of spatial positions 525 on the voltage sensitive chromophore surface 130. In this case, either the surface holder 505 or the fluorescence sensing system 515 can be moved in a scanning path in order to sense the surface fluorescence emission spectra 140 at the different positions. In such configurations, the analysis system 520 can be used to analyze the plurality of surface fluorescence emission spectra 140 to evaluate a uniformity of a characteristic of the voltage sensitive chromophore surface 130. This can be useful for a number of applications, including detecting surface defects or inspecting features on the surface.

There are a wide variety of applications that involve depositing a pattern of features onto a surface, including the fabrication of electrical components or devices (e.g., on a silicon wafer or on a glass or polymer substrate). In some cases, it can be difficult to inspect such components, particularly when they may include features that are fabricated using transparent, or partially transparent, materials. Such features may not be easily detected by conventional machine vision inspection techniques that involve capturing an image of the surface using visible light. However, the presence of the features will produce local perturbations in the interfacial electric field of the surface. These perturbations can be detected using methods in accordance with embodiments of the present invention by applying a monolayer of voltage sensitive chromophore to the surface and measuring the fluorescence emission spectrum. The presence of edges and surface textures on the surface can also affect the amplitude and direction of the emitted fluorescent light. Such perturbations can be detectable with appropriate types of sensors.

In one such embodiment, the surface 100 having the features thereon is treated to attach a monolayer of the voltage sensitive chromophore 152 (FIG. 2B) providing the voltage sensitive chromophore surface 130 as described above relative to FIG. 1. The surface evaluation system 500 can then be used to measure a pattern of fluorescent light as a function of spatial position on the voltage sensitive chromophore surface 130. In an exemplary configuration, the pattern of fluorescent light can be characterized by measuring the surface fluorescence emission spectra 140 at a lattice of spatial positions 525 as described above. In other configurations, the pattern of fluorescent light can be characterized by measuring an intensity or a color (or some other attribute) of the fluorescent light. In such cases, the fluorescence sensing system 515 does not necessarily need to determine the surface fluorescence emission spectra 140, but rather can directly measure the fluorescent light characteristic using other types of measurements (e.g., intensity measurements or color measurements).

The analysis system 520 can analyze the measured pattern of fluorescent light in order to inspect the surface. In some embodiments, features in the measured pattern of fluorescent light can be compared to a reference pattern associated with the device being fabricated, for example to verify that there are no shorts or voids in a pattern of micro-wires. In some embodiments, the measured pattern of fluorescent light can be analyzed to detect surface defects (e.g., non-uniformities in a surface region that was supposed to be uniform).

When the surface evaluation system 500 is being used to measure a pattern of fluorescent light, it may not be necessary to measure the fluorescent light while the voltage sensitive chromophore surface 130 is in contact with a liquid 132, particularly if the goal is to detect non-uniformities or other defects rather than determining quantitative interfacial electric field intensities. In such cases, the pattern of fluorescent light can be measured when the voltage sensitive chromophore surface 130 is exposed to air (or some other gas).

The methods described herein have many advantages compared to other methods for using voltage sensitive chromophores currently used in the art. The describes methods provide a chromophore that is covalently attached to the surface. In contrast, other methods, such as those described in the aforementioned articles by Loew and Pope et al., use chromophores embedded in membranes or self-assembled monolayers. In such arrangements, the location of the chromophore is not known precisely, nor is the measured fluorescence emission spectra guaranteed to be from a chromophore in a known position with respect to the surface or membrane, but can be mixed with the spectra of unembedded chromophore molecules and chromophore molecules at various distances from the surface. In the methods of the present invention, the voltage sensitive chromophore is attached to the surface in a known way, and is created only when it is attached to the surface, so the position of the chromophore is known precisely.

Another advantage of the present invention is that it can be used with a wide variety of different surfaces including silica, polymer, metal, inorganic, and other surfaces. Other methods have restrictions on the sample surface, such as requiring a biological membrane a metal surface or a metal electrode. For example, the method described in the aforementioned articles by Pope et al. require that the surface be a metal electrode, and specifically a silver electrode, in order to enhance the fluorescence of the chromophore. Our method has been shown to work without metal-enhanced fluorescence.

In other methods, such as those described in the aforementioned articles by Pope et al., external fields need to be applied (for example, to an electrode surface or a membrane surface) to provide a change in the electric field to induce a Stark shift, which is measured by a shift in the fluorescence emission spectrum. In methods of the present invention, the emission of the chromophore on the surface is compared to the emission of the chromophore in solution, which enables the Stark shift to be determined and the interfacial electric field to be calculated without the use of any applied field. This makes the measurement dependent only on the voltage sensitive chromophore, the surface, and the liquid, and is not dependent on any applied fields.

Because the methods in this application do not require applied fields, the methods are simpler and do not require the use of more complicated instrumentation. Additionally, the methods can be applied over a large area, and need not be confined to smaller areas, such as in atomic force microscopy.

Furthermore, the methods are non-destructive for the sample, and only require that the surface be modified to include the voltage sensitive chromophore. In other methods for determining an interfacial electric field, such as the streaming potential method described in the aforementioned article by Xie et al. and the atomic force microscopy method described in the aforementioned article by Li et al., the sample is significantly changed, and may not be used for any other testing.

Generally, the methods of the present invention are simpler, more precise, more accurate, and more versatile than prior art methods for measuring interfacial electric fields. Furthermore, the present methods can be used to characterize large areas of a surface, and to provide a sensor for characterizing a liquid.

The invention has been described in detail with particular reference to certain preferred embodiments thereof, but it will be understood that variations and modifications can be effected within the spirit and scope of the invention.

PARTS LIST 100 surface
105 linking group
110 first reaction
112 covalent linkage
115 surface with linking group
120 voltage sensitive chromophore precursor
125 second reaction
130 voltage sensitive chromophore surface
132 liquid
135 measure surface fluorescence emission spectrum step
140 surface fluorescence emission spectrum
145 chromophore component
147 coupling agent
150 third reaction
152 voltage sensitive chromophore
155 voltage sensitive chromophore solution
160 measure solution fluorescence emission spectrum step 165 solution fluorescence emission spectrum
170 determine interfacial electric field intensity step
175 interfacial electric field intensity
180 p-substituted dialkylamino aryl group
182 conjugate linkage
185 N-containing heterocyclic aromatic group
200 determine characteristic of liquid step
205 liquid characteristic
210 first liquid
215 second liquid
220 measure first fluorescence emission spectrum step
225 first fluorescence emission spectrum
230 measure second fluorescence emission spectrum step
235 second fluorescence emission spectrum
240 characterize difference between liquids step
245 difference between the liquids
300 graph
310 graph
320 graph
340 transperiplanar rotomer
350 ground state
352 ground state energy level
360 exited state
362 exited state energy level
364 exited solution state energy level
400 graph
410 curve
420 graph
430 first wavelength
435 second wavelength
500 surface evaluation system
505 surface holder
510 irradiation source
515 fluorescence sensing system
520 analysis system
525 lattice of spatial positions

The invention claimed is:

1. A method for measuring an interfacial electric field intensity, comprising:
providing a surface having a reactive carbocyclic aromatic linking group covalently attached thereon;
providing a voltage sensitive chromophore precursor including a p-substituted dialkylamino aryl group that is conjugatively linked to a terminal N-containing heterocyclic aromatic group;
reacting the voltage sensitive chromophore precursor with the reactive carbocyclic aromatic linking group that is covalently attached to the surface to form a monolayer of a voltage sensitive chromophore that is covalently bound to the surface;
irradiating the monolayer of the covalently bound voltage sensitive chromophore with actinic radiation while it is in contact with a liquid and measuring a first fluorescence emission spectrum;
providing a voltage sensitive chromophore solution of the voltage sensitive chromophore dissolved in a sample of the liquid;
irradiating the voltage sensitive chromophore solution with actinic radiation and measuring a second fluorescence emission spectrum; and
comparing the first and second fluorescence emission spectra to determine an interfacial electric field intensity, wherein comparing the first and second fluorescence emission spectra includes performing a mathematical analysis to determine at least one parameter characterizing a difference between the first and second fluorescence emission spectra, and wherein the interfacial electric field intensity is determined responsive to the determined at least one parameter.

2. The method of claim 1, wherein the reactive carbocyclic aromatic linking group includes a benzyl halide group.

3. The method of claim 1, wherein the N-containing heterocyclic aromatic group is a pyridinyl group.

4. The method of claim 1, wherein the voltage sensitive chromophore is a reaction product where the reactive carbocyclic aromatic linking group is bonded to the terminal N-containing heterocyclic aromatic group of the voltage sensitive chromophore precursor.

5. The method of claim 1, wherein the liquid is acetone, methanol, water or chloroform.

6. The method of claim 1, wherein comparing the first and second fluorescence emission spectra includes:
determining a first spectral peak for the first fluorescence emission spectrum;
determining a second spectral peak for the second fluorescence emission spectrum; and
determining a difference parameter representing a wavelength difference or a wave number difference between the first and second spectral peaks; wherein the interfacial electric field intensity is determined responsive to the difference parameter.

7. The method of claim 1, wherein comparing the first and second fluorescence emission spectra includes:
specifying first and second wavelengths;
determining a first intensity ratio parameter representing a first intensity ratio between a value of the first fluorescence emission spectrum at the first wavelength and a value of the first fluorescence emission spectrum at the second wavelength;
determining a second intensity ratio parameter representing a second intensity ratio between a value of the second fluorescence emission spectrum at the first wavelength and a value of the second fluorescence emission spectrum at the second wavelength; and
wherein the interfacial electric field intensity is determined responsive to the first and second intensity ratio parameters.

8. The method of claim 1, wherein the surface having the reactive carbocyclic aromatic linking group covalently attached thereon is formed by:
providing a solution including the reactive carbocyclic aromatic linking group;
providing a surface capable of reacting with the reactive aromatic linking group; and
bringing the solution into contact with the surface, thereby reacting the reactive carbocyclic aromatic linking group with the surface to attach the reactive carbocyclic aromatic linking group to the surface with a covalent linkage.

9. The method of claim 1, wherein the surface is a silica surface or a polymer surface.

10. The method of claim 1, wherein the surface is non-biological.

* * * * *